(12) United States Patent
Etemad et al.

(10) Patent No.: US 9,770,179 B2
(45) Date of Patent: Sep. 26, 2017

(54) SYSTEM, METHOD AND DEVICE FOR DETECTING HEART RATE

(71) Applicant: GestureLogic Inc., Ottawa (CA)

(72) Inventors: Seyed Ali Etemad, Ottawa (CA); Leonard MacEachern, Ottawa (CA); Mark Klibanov, Ottawa (CA); Roshanak Houmanfar, Ottawa (CA)

(73) Assignee: GestureLogic Inc., Ottawa (CA)

( * ) Notice: Subject to any disclaimer, the term of this patent is extended or adjusted under 35 U.S.C. 154(b) by 0 days.

(21) Appl. No.: 14/669,635

(22) Filed: Mar. 26, 2015

(65) Prior Publication Data
US 2015/0272457 A1    Oct. 1, 2015

Related U.S. Application Data

(60) Provisional application No. 61/970,477, filed on Mar. 26, 2014, provisional application No. 61/970,482, filed on Mar. 26, 2014.

(51) Int. Cl.
*A61B 5/04* (2006.01)
*A61B 5/024* (2006.01)
(Continued)

(52) U.S. Cl.
CPC ........ *A61B 5/02438* (2013.01); *A61B 5/0245* (2013.01); *A61B 5/04017* (2013.01);
(Continued)

(58) Field of Classification Search
CPC .............. A61B 5/0245; A61B 5/04017; A61B 5/02438
(Continued)

(56) References Cited

U.S. PATENT DOCUMENTS 8,909,332 B2   12/2014   Vitali et al.
9,510,789 B2   12/2016   Houmanfar et al.
(Continued)

FOREIGN PATENT DOCUMENTS

CA   2818020 A1   12/2012
EP   2698099 A1    2/2014
(Continued)

OTHER PUBLICATIONS

Duda et al., Pattern Classification (2nd Edition), Wiley-Interscience, 2000.
(Continued)

*Primary Examiner* — Amanda Patton
*Assistant Examiner* — Philip C Edwards
(74) *Attorney, Agent, or Firm* — Bereskin & Parr LLP/S.E.N.C.R.L., s.r.l.

(57) ABSTRACT

A system, method and device are described for detecting a heart rate. A sensing unit can have a skin-facing surface that is removably securable to a user's skin surface and include at least one sensor positioned to acquire a bio-signal from the skin surface. A controller can be configured to capture a bio-signal stream using the at least one sensor and generate a preprocessed bio-signal stream by band-pass filtering the captured bio-signal stream with a predetermined passband. The controller can also be configured to determine, in a moving window, heartbeat signal portions when the preprocessed bio-signal stream has heartbeat impulse characteristics and determine the time between adjacent heartbeat signal portions to compute the heart rate.

20 Claims, 12 Drawing Sheets

(51) Int. Cl.
*A61B 5/0245* (2006.01)
*A61B 5/0408* (2006.01)
*A61B 5/00* (2006.01)

(52) U.S. Cl.
CPC ........ *A61B 5/04085* (2013.01); *A61B 5/6801* (2013.01); *A61B 5/0006* (2013.01); *A61B 5/725* (2013.01)

(58) Field of Classification Search
USPC ....................................................... 600/509
See application file for complete search history.

(56) References Cited

U.S. PATENT DOCUMENTS

| | | | |
|---|---|---|---|
| 2005/0113703 A1* | 5/2005 | Farringdon .......... | A61B 5/0428 600/509 |
| 2005/0177059 A1 | 8/2005 | Koivumaa et al. | |
| 2011/0301441 A1 | 12/2011 | Bandic et al. | |
| 2012/0071743 A1 | 3/2012 | Todorov et al. | |
| 2012/0271121 A1 | 10/2012 | Della Torre et al. | |
| 2014/0278229 A1 | 9/2014 | Hong et al. | |
| 2014/0288435 A1 | 9/2014 | Richards et al. | |
| 2015/0133823 A1 | 5/2015 | Houmanfar et al. | |
| 2015/0272482 A1 | 10/2015 | Houmanfar et al. | |
| 2015/0272483 A1 | 10/2015 | Etemad et al. | |
| 2015/0272501 A1 | 10/2015 | MacEachern et al. | |
| 2016/0206921 A1 | 7/2016 | Szabados et al. | |
| 2016/0213323 A1 | 7/2016 | Proud | |

FOREIGN PATENT DOCUMENTS

| | | |
|---|---|---|
| WO | 2006053290 A2 | 5/2006 |
| WO | 2009152608 A1 | 12/2009 |

OTHER PUBLICATIONS

Gelman, "Analysis of Variance—Why It Is More Important Than Ever", Annals of Statistics, vol. 33 (1), pp. 1-53, 2005.
Kulić et al., "Incremental Learning of Full Body Motion Primitives and Their Sequencing Through Human Motion Observation", The International Journal of Robotics Research. SAGE Publications, 0278364911426178, 2011.
Rabiner, "A Tutorial on Hidden Markov Models and Selected Applications in Speech Recognition", Proceedings of the IEEE, vol. 77 (2), pp. 257-286, 1989.
Smith, A Tutorial on Principal Components Analysis, 2002.
Wang, "Recent Developments in Human Motion Analysis." Pattern Recognition, vol. 36 (3), pp. 585-601, Elsevier, 2003.
Lin et al., "Full-Body Multi-Primitive Segmentation Using Classifiers", Humanoid Robotics, Proceedings of the 14th RAS International Conference, IEEE, pp. 874-880, 2014.
Document relating to PCT Application No. PCT/CA2016/050346, dated Jul. 19, 2016 (International Search Report & Written Opinion).
Document relating to PCT Application No. PCT/CA2016/050347, dated Jun. 8, 2016 (International Search Report & Written Opinion).
Lin, Chia-Hua, "A Real-Time Human Posture Classifier and Fall-Detector," Electronic Thesis or Dissertation, Case Western Reserve University, Aug. 2014, OhioLINK Electronic Theses and Dissertations Center, pp. 1-30 (*pp. 7-8, 6, 12-13, 19-21, 26-26, 32, 49, 66).
Quwaider, Muhannad and Subir Biswas, "Body posture identification using hidden Markov model with a wearable sensor network," Bodynets (2008).
Document relating to PCT Application No. PCT/CA2016/050348, dated Jun. 30, 2016 (International Search Report & Written Opinion).
Document relating to U.S. Appl. No. 14/669,689, dated Mar. 6, 2017 (Office Action).
Document relating to U.S. Appl. No. 14/669,726, dated Mar. 3, 2017 (Office Action).
Document relating to PCT Application No. PCT/CA2016/050345, dated May 18, 2016 (International Search Report & Written Opinion).
Document relating to U.S. Appl. No. 14/669,781, dated May 11, 2016 (Office Action).
Document relating to U.S. Appl. No. 14/669,781, dated Dec. 16, 2016 (Final Office Action).
Document relating to U.S. Appl. No. 14/669,726, dated Jul. 21, 2017 (Final Office Action). Retrieved from PAIR.
Chen et al., "Hand gesture recognition research based on surface EMG sensors and 2D-accelerometers," 11th IEEE International Symposium on Wearable Computers, 2007.
Shin et al., "Developing a device using accelerometeres and EMG for hand movement recognition," 6th International Conference on Biomedical Engineering and Informatics, pp. 398-402, 2013.
Georgakis et al., "Fatigue analysis of the surface EMG Signal in isometric constant force contractions using the average instantaneous frequency," IEEE Transactions on Biomedical Engineering, vol. 50, No. 2, pp. 262-265, 2003.
Pogorelc et al., "Home-based health monitoring of the elderly through gait recognition," Journal of Ambient Intelligence and Smart Enviroments, vol. 4, No. 5, Abstract, 2012.
Chen et al., "Sensing strides using EMG signal for pedestrian navigation, " GPS Solutions, vol. 15, No. 2, pp. 161-170, 2011.
Document relating to U.S. Appl. No. 14/669,689, dated Jul. 21, 2017 (Final Office Action). Retrieved from Public PAIR.
Altun et al., "Comparative study on classifying human activities with miniature inertial and magnetic sensors," Pattern Recognition, v. 43, pp. 3605-3620, 2010.
Avci et al., "Activity recognition using inertial sensing for healthcare, wellbeing and sports applications: A survey," 23rd International Conference on Architecture of Computing Systems, 2010.
Tapia et al., "Real-time recognition of physical activities and their intensities using wireless accelerometers and a heart rate monitor," 11th IEEE International Symposium on Wearable Computers, 2007.

\* cited by examiner

SYSTEM, METHOD AND DEVICE FOR DETECTING HEART RATE

CROSS-REFERENCE TO RELATED APPLICATIONS

This application claims the benefit of U.S. Provisional Patent Application No. 61/970,477, filed Mar. 26, 2014 and U.S. Provisional Patent Application No. 61/970,482, filed Mar. 26, 2014. The entire contents of U.S. Provisional Patent Application Nos. 61/970,477 and 61/970,482 are hereby incorporated by reference.

FIELD

The various embodiments described herein generally relate to systems, methods and devices for detecting a user's heart rate. In particular, the embodiments relate to detecting a user's heart rate from bio-signals acquired from the user's skin surface.

BACKGROUND

Wearable computing systems and devices are an emerging category of consumer products. These devices enable users to perform a variety of tasks. For example, users may virtually interact with online account; record and/or observe information such as videos, images, and sounds; control other computing systems and other connected appliance; interact with other people; and in some instances monitor the current conditions of an individual's body.

Devices capable of monitoring an individual's fitness are becoming increasingly popular. Monitoring and maintaining physical fitness is an ongoing concern for individuals with busy lifestyles, and this concern is becoming more pronounced with an aging population. As a result, demand is increasing for devices that can track physical activities and individual fitness.

Various types of devices can be used to track an individual's physiological responses to various activities, such as exercise. While some devices are limited to use in laboratories and hospitals, portable/wearable devices for tracking physiological responses are being developed that can be worn by individuals at various locations on the individual's body. Often, these wearable devices may be positioned at locations other than on the individual's chest, for example when tracking muscle activity in various regions. Such devices may benefit from a method of determining an individual's heart rate that does not rely on the use of a chest strap or transthoracic measurements in general.

SUMMARY OF VARIOUS EMBODIMENTS

In a broad aspect, at least one embodiment described herein provides a system for detecting a heart rate. The system can include a sensing unit and a controller operatively coupled to the sensing unit. The sensing unit can have a skin-facing surface removably securable to a user skin surface and at least one sensor positioned to acquire a bio-signal from the skin surface. The controller can be configured to capture a bio-signal stream using the at least one sensor, generate a preprocessed bio-signal stream by band-pass filtering the captured bio-signal stream with a predetermined passband. The controller can also be configured to in a moving window, determine heartbeat signal portions when the preprocessed bio-signal stream has heartbeat impulse characteristics, and determine time between adjacent heartbeat signal portions to compute the heart rate.

In some embodiments, the heartbeat signal portions can be determined by applying a detection algorithm to the filtered bio-signal stream to generate. In some embodiments, the detection algorithm uses parameters of a supervised system trained using a plurality of captured bio-signal streams.

In some embodiments, the heartbeat impulse characteristics can include the signal portion having spatiotemporal properties indicative of a heartbeat impulse.

In some embodiments, the heartbeat impulse characteristics can include the signal portion exceeding a threshold value.

In some embodiments, the threshold value can be determined using the amplitude of the preprocessed bio-signal stream in the moving window.

In some embodiments, the threshold value can be determined as one of a midpoint value, a mean value, a midpoint value, a mean value, a median value, a minimum value, a maximum value, a linear function, and a non-linear function of the amplitude of the preprocessed bio-signal stream in the moving window, or some combination thereof.

In some embodiments, the time between adjacent signal portions can be determined by segmenting the preprocessed bio-signal stream into heartbeat signal portions having heartbeat impulse characteristics and signal portions not having heartbeat impulse characteristics and determining the time between adjacent impulses.

In some embodiments, the passband can have an upper cutoff frequency in a range between 10 Hz and 18 Hz.

In some embodiments, the passband can have a lower cutoff frequency in a range between 3 Hz and 5 Hz.

In some embodiments, the sensors can be electrodes. The electrodes may be passive electrodes in some embodiments. In some embodiments, the electrodes may be active electrodes.

In some embodiments, the at least one sensor includes two sensors. In some embodiments, the sensors are positioned to acquire a differential bio-signal from the skin surface. In some embodiments, the sensors can be positioned cross-body.

In a broad aspect, at least one embodiment described herein provides a method for detecting a heart rate using a sensing unit having at least one sensor positioned to acquire a bio-signal from the skin surface. The method can include capturing a bio-signal stream using the at least one sensor and generating a preprocessed bio-signal stream by band-pass filtering the captured bio-signal stream with a predetermined passband. The method can further include determining, in a moving window, heartbeat signal portions when the preprocessed bio-signal stream has heartbeat impulse characteristics, and determining time between adjacent heartbeat signal portions to compute the heart rate.

In a broad aspect, at least one embodiment described herein provides a wearable device for detecting a heart rate. The wearable device can have a skin-facing surface removably securable to a user skin surface, at least one sensor positioned to acquire a bio-signal from the skin surface, and a controller operatively coupled to the at least one sensor. The controller can be configured to capture a bio-signal stream using the at least one sensor and generate a preprocessed bio-signal stream by band-pass filtering the captured bio-signal stream with a predetermined passband. The controller can also be configured to determine, in a moving window, heartbeat signal portions when the preprocessed bio-signal stream has heartbeat impulse characteristics, and determine time between adjacent heartbeat signal portions to compute the heart rate.

In yet another broad aspect, at least one embodiment described herein provides a non-transitory computer readable medium storing computer-executable instructions, which, when executed by a computer processor, cause the computer processor to carry out a method of detecting a heart rate wherein the method is defined herein.

BRIEF DESCRIPTION OF THE DRAWINGS

For a better understanding of the various embodiments described herein, and to show more clearly how these various embodiments may be carried into effect, reference will be made, by way of example, to the accompanying drawings which show at least one example embodiment, and which are now briefly described.

Figure 1:
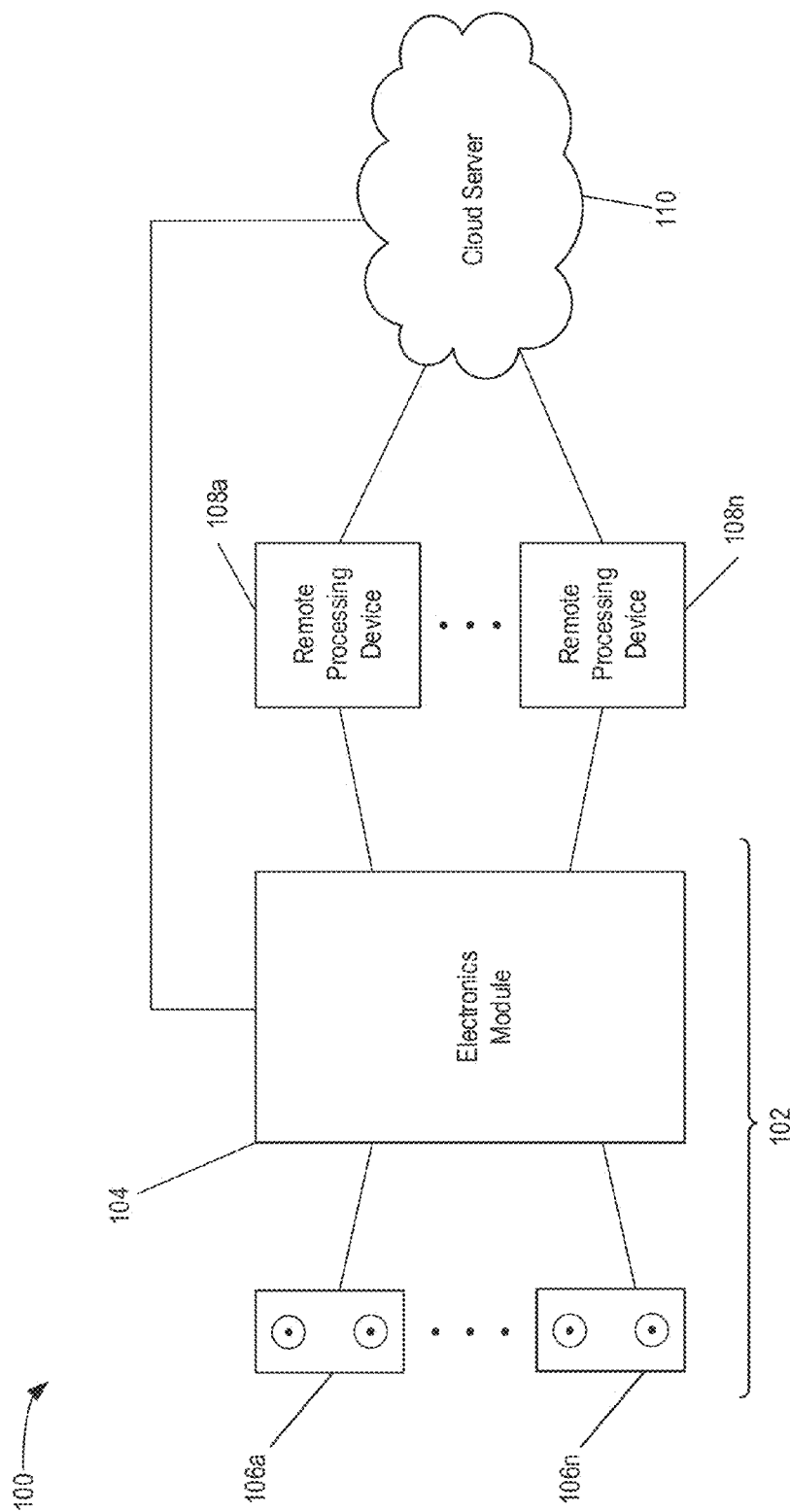
FIG. 1 is a block diagram illustrating an example embodiment of a system for determining a user's heart rate.

Further aspects and features of the embodiments described herein will appear from the following description taken together with the accompanying drawings.

DETAILED DESCRIPTION OF THE EMBODIMENTS

Various systems or methods will be described below to provide an example of an embodiment of the claimed subject matter. No embodiment described below limits any claimed subject matter and any claimed subject matter may cover methods or systems that differ from those described below. The claimed subject matter is not limited to systems or methods having all of the features of any one system or method described below or to features common to multiple or all of the apparatuses or methods described below. It is possible that a system or method described below is not an embodiment that is recited in any claimed subject matter. Any subject matter disclosed in a system or method described below that is not claimed in this document may be the subject matter of another protective instrument, for example, a continuing patent application, and the applicants, inventors or owners do not intend to abandon, disclaim or dedicate to the public any such subject matter by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

It should also be noted that the terms "coupled" or "coupling" as used herein can have several different meanings depending in the context in which these terms are used. For example, the terms coupled or coupling can have a mechanical, electrical or communicative connotation. For example, as used herein, the terms coupled or coupling can indicate that two elements or devices can be directly connected to one another or connected to one another through one or more intermediate elements or devices via an electrical element, electrical signal or a mechanical element depending on the particular context. Furthermore, the term "communicative coupling" may be used to indicate that an element or device can electrically, optically, or wirelessly send data to another element or device as well as receive data from another element or device.

It should also be noted that, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that terms of degree such as "substantially", "about" and "approximately" as used herein mean a reasonable amount of deviation of the modified term such that the end result is not significantly changed. These terms of degree may also be construed as including a deviation of the modified term if this deviation would not negate the meaning of the term it modifies.

Furthermore, any recitation of numerical ranges by endpoints herein includes all numbers and fractions subsumed within that range (e.g. 1 to 5 includes 1, 1.5, 2, 2.75, 3, 3.90, 4, and 5). It is also to be understood that all numbers and fractions thereof are presumed to be modified by the term "about" which means a variation of up to a certain amount of the number to which reference is being made if the end result is not significantly changed.

Described herein are systems, methods and devices for detecting an individual's heart rate. The described embodiments can use wearable devices to measure, monitor, and report a user's heart rate for a variety of uses such as determining biometrics for that individual. For example, an individual's heart rate may be used to determine the energy expenditure for that individual, often in combination with other information such as demographic data (e.g. age, sex, weight, and height). The individual's heart rate, and other biometrics derived therewith can be used for tracking and monitoring the individual's biometric features for medical, fitness, athletic, entertainment or other purposes.

The example embodiments of the systems, methods, and devices described herein may be implemented as a combination of hardware or software. In some cases, the example embodiments described herein may be implemented, at least in part, by using one or more computer programs, executing on one or more programmable devices comprising at least one processing element, and a data storage element (including volatile and non-volatile memory and/or storage elements). These devices may also have at least one input device (e.g. a pushbutton keyboard, mouse, a touchscreen, and the like), and at least one output device (e.g. a display screen, a printer, a wireless radio, and the like) depending on the nature of the device.

It should also be noted that there may be some elements that are used to implement at least part of one of the embodiments described herein that may be implemented via software that is written in a high-level procedural language such as object oriented programming. Accordingly, the program code may be written in C, C++ or any other suitable programming language and may comprise modules or classes, as is known to those skilled in object oriented programming. Alternatively, or in addition thereto, some of these elements implemented via software may be written in assembly language, machine language or firmware as needed. In either case, the language may be a compiled or interpreted language.

At least some of these software programs may be stored on a storage media (e.g. a computer readable medium such as, but not limited to, ROM, magnetic disk, optical disc) or a device that is readable by a general or special purpose programmable device. The software program code, when read by the programmable device, configures the programmable device to operate in a new, specific and predefined manner in order to perform at least one of the methods described herein.

Furthermore, at least some of the programs associated with the systems and methods of the embodiments described herein may be capable of being distributed in a computer program product comprising a computer readable medium that bears computer usable instructions for one or more processors. The medium may be provided in various forms, including non-transitory forms such as, but not limited to, one or more diskettes, compact disks, tapes, chips, and magnetic and electronic storage. In alternative embodiments, the medium may be transitory in nature such as, but not limited to, wire-line transmissions, satellite transmissions, internet transmissions (e.g. downloads), media, digital and analog signals, and the like. The computer useable instructions may also be in various formats, including compiled and non-compiled code.

Figure 3A:
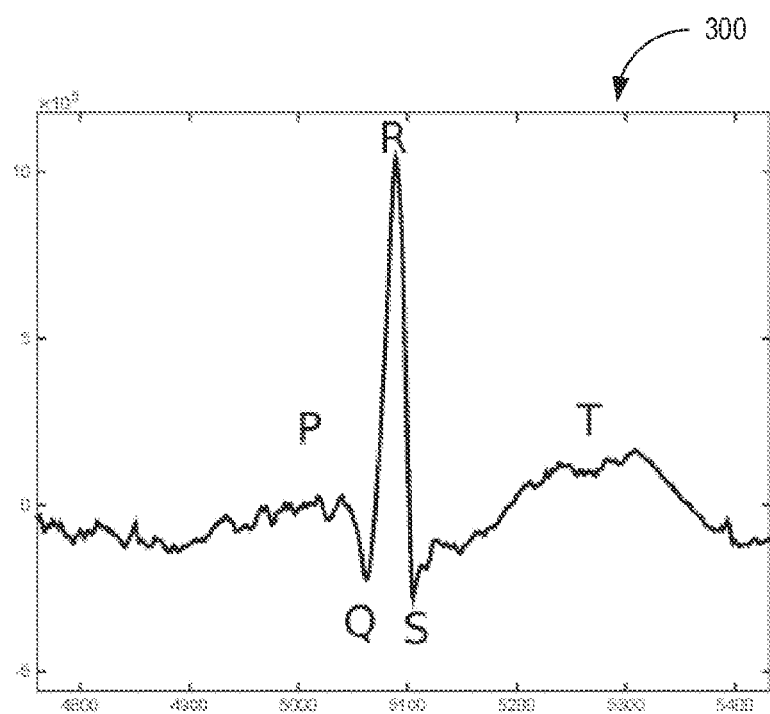
FIG. 3A is a diagram illustrating a plot of an example of a heart beat PQRST complex.

The embodiments described herein generally provide methods for detecting electrical signals or impulses corresponding to heart beat impulses in bio-signals collected from a user's body using one or more sensors. The electrical impulses from the heart produce a distinctive waveform, portions of which may be detectable even in the presence of high levels of noise or other undesired signal components (an example waveform is shown in FIG. 3A, discussed below). These heartbeat impulse signals propagate throughout an individual's entire body. Electrical bio-signals that include signal components from the heartbeat impulses can be captured using one or more sensors positioned near the user's skin surface. The captured bio-signals can then be analyzed to detect the electrical impulses generated by the polarization and depolarization of the cardiac muscle.

The electrical bio-signals acquired using sensors on a user's skin surface are often highly contaminated by noise signals such as other electrical signals generated by the human body and environmental noise. For example, voluntary or involuntary muscles contractions may generate electrical signals (electromyography signals) that interfere with the signals from the heartbeat impulses. Environmental noise signals (such as 60 Hz power line "hum"), body produced signals (e.g. from muscle contractions), and noise signals from electronics of the wearable device can also interfere with the signals generated by heartbeat impulses. Surface bio-signal measurements may also be prone to "motion artifact" noise, which results from the displacement of the sensors relative to muscles underlying the sensors. Accordingly, bio-signals acquired using sensors near the user's skin surface may be processed to remove undesired components and then analyzed to detect the signal components corresponding to, or indicative of, the heartbeat impulse.

The systems described herein may include a sensing unit having a skin-facing surface removably securable to a user's skin surface. The sensing unit can have at least one sensor positioned to acquire a bio-signal from the skin surface. For example, the sensor may be a contact sensor such as an electrode (passive or active) positioned to make contact with the skin surface and acquire an electrical bio-signal from the user skin surface. The electrode can be made of various materials such as metal, electrically conductive fabrics, gels, and conductive polymers among others. Non-contact sensors may also be used, such as infrared sensors, ultrasound sensors, visual sensors, and capacitively coupled sensors for example. In some embodiments, non-contact sensors such as infrared-sensors can be used in combination with the methods described herein for detecting heart rate using acquired bio-signal. This may increase accuracy and confidence in the detected heart rate.

The sensing unit can be operatively coupled to a controller. In some embodiments, the sensing unit and the controller may both be provided in a wearable device. In other embodiments, the sensing unit may be provided in a wearable system coupled to a communication module configured to communicate with a remote controller.

The communication module may be a wireless communication module configured to communicate with a remote processing device such as a mobile device. The communication module may transmit signals acquired by the sensing unit to the controller using various communication protocols such as Bluetooth, Bluetooth Low-Energy, WiFi, ANT+, etc. The controller may then process the received signal to determine the user's heart rate. In some cases, the controller may be coupled to the communication module (and thereby the sensing unit) using a wired connection such as Universal Serial Bus (USB) or other port.

Regardless of where it is physically located, the controller can be configured to capture a bio-signal stream using the sensors of the sensing unit. The controller can then generate a preprocessed bio-signal stream by band-pass filtering the captured bio-signal stream with a predetermined passband. The passband may be selected based on a frequency range expected to minimize contributions from undesired signals, such as electromyography (EMG), noise signals, and motion artifact.

The passband may be selected to reject or minimize undesirable high frequency components such as environmental noise (e.g. due to 60 Hz power line hum) and EMG signals. Typically, EMG signals may be found at frequencies greater than 15 Hz to 20 Hz. The upper cut-off frequency can be selected to minimize the amount of noise from EMG signals and other higher frequency noise signals. Undesirable low frequency components such as motion artifacts may also be removed or minimized by such a passband. Typically, motion artifact noise signals have a frequency of 1 Hz or 2 Hz. The lower cut-off frequency can be selected to minimize the amount of motion artifact noise found in the filtered bio-signals. For example, the passband may have a lower cutoff frequency of in a range between 3 Hz and 5 Hz and an upper cut-off frequency of in a range from 10 Hz to 18 Hz. In some cases, the lower cut-off frequency may be selected as approximately 3 Hz. In some cases, the upper cut-off frequency may be selected as approximately 10 Hz.

In some cases, the band-pass filtering may be achieved using a two-step filtering procedure, where a high pass filter (with a cut-off frequency equivalent to the lower cutoff frequency of the passband) and a low pass filter (with a cut-off frequency equivalent to the upper cutoff frequency of the passband) can be applied to the captured bio-signal stream.

The controller can also be configured to use a moving window to determine heartbeat signal portions of the preprocessed bio-signal stream that have heartbeat impulse characteristics. The heartbeat signal portions can be determined using supervised or unsupervised heartbeat detection methods. Generally, supervised heartbeat detection methods refer to detection systems or algorithms that have been trained using captured electrical bio-signals where the heartbeat signal portions have been identified.

In some cases, the heartbeat impulse characteristics may be that the signal portion exceeds a threshold value. A threshold value may be predetermined or determined based on the values of the preprocessed bio-signal stream in the moving window. In other cases, the heartbeat impulse characteristics may be that the signal portion has a similar shape, or similar spatiotemporal properties to a heartbeat impulse signal. Spatiotemporal properties generally refer to properties that can define the spatial and/or temporal characteristics of a signal. Examples of spatiotemporal properties include a signal maximum, signal minimum, signal mean, signal median, standard deviation, width etc.

For example, a matched filter may be used to identify signal portions having heartbeat impulse characteristics. In other embodiments, using a moving window, a correlation coefficient of the moving window can be determined with respect to a template of a heartbeat impulse signal, for example the PQRST complex or a subset thereof. The controller may then determine the time between adjacent signal portions to compute the heart rate.

Referring now to FIG. 1, shown therein is a block diagram illustrating an example embodiment of a system 100 that can be used to detect a user's heart rate. System 100 includes a wearable unit 102, one or more remote processing devices 108 and a remote cloud server 110.

Wearable unit 102 includes a sensing unit removably securable to a user skin surface with a skin-facing surface of the sensing unit positioned to make contact with the skin surface. The sensing unit can generally be provided in a wearable unit 102 that includes one or more wearable devices that can be manufactured of various materials such as fabric, cloth or polymer materials suitable for being worn in contact with a user's skin for example. A portion, or all, of the wearable devices can be made of breathable materials to increase comfort while a user is performing an activity.

In some embodiments, the wearable devices may be formed into a garment or form of apparel such as a band, shirts, shorts, and sleeves for example. In some cases, wearable devices may be a compression garment manufactured from a material that is compressive. A compression garment may minimize the impact from "motion artifacts" by reducing the relative movement of the wearable device with respect to a target muscle. In some cases, the wearable devices may also include anti-slip components on the skin-facing surface. For example, a silicone grip may be provided on the skin-facing surface of the wearable devices to further reduce the potential for motion artifacts. In some cases, the weave of a compression garment textile can be optimized to minimize motion artifacts by reducing motion in preferred directions of the textile weave. For example, additional compression (in addition to the compression elsewhere in the garment) can be added to a compression garment in locations having sensors.

The wearable devices can be manufactured of an elastic or compressive material, such as neoprene, elastane or the like. In other embodiments, the wearable devices may be manufactured of non-compressive material. In some cases, a wearable device may include an alignment guide to indicate the optimal orientation of the wearable device when being worn.

The sensing unit includes a plurality of sensors 106a-106n positioned to acquire an electrical signal from the user's skin surface. In some embodiments, the sensors 106 can be integrated into the material of one or more wearable devices. Alternatively, the sensors 106 can be affixed or attached to the wearable devices, e.g. printed, glued, laminated or ironed onto the skin-facing surface of the sensing unit. In some cases, the sensors 106 may be provided as an iron-on component that a user can then apply to a wearable device. Various other methods of affixing the sensors 106 to the wearable devices may also be used.

Various different sensors 106 may be used in the sensing unit. For example, the sensors 106 may be electrodes (active or passive) made from metals, conductive polymers, conductive inks, or conductive textiles for example. In some cases, the sensors 106 may include non-contact sensors such as infrared sensors, ultrasound sensors, visual sensors, and capacitively coupled sensors for example.

The wearable unit 102 can also include an electronics module 104 coupled to the plurality of sensors 106. In some cases, the electronics module 104 can include a power supply, a controller, a memory, a signal acquisition unit operatively coupled to the controller and to the plurality of sensors 106, and a wireless communication module operatively coupled to the controller.

Generally, the sensing unit refers to the plurality of sensors 106 and the signal acquisition unit. The signal acquisition unit may provide initial analog processing of signals acquired using the sensors 106, such as amplification. The signal acquisition unit may also include an analog-to-digital converter to convert the acquired electrical bio-signals from the continuous time domain to a discrete time domain. The analog-to-digital converter may then provide the digitized electrical bio-signals to the controller for further analysis or for communication to a remote processing device 108 or remote cloud server 110 for further analysis. In embodiments where multiple wearable devices are used to detect a user's heart rate, one or more of the multiple wearable devices may include a controller that performs the signal processing and analysis.

The electronics module 104 of the wearable unit 102 can be communicatively coupled to one or more remote processing devices 108a-108n, e.g. using a wireless communication module (e.g., Bluetooth, IEEE 802.11, etc.). The remote processing devices 108 can be any type of processing device such as a personal computer, a tablet, and a mobile device such as a smartphone or a smartwatch for example. The electronics modules 104 can also be communicatively coupled to the remote cloud server 110 over, for example, a wide area network such as the Internet.

Each remote processing device 108 and remote cloud server 110 typically includes a processing unit, a display, a user interface, an interface unit for communicating with other devices, Input/Output (I/O) hardware, a wireless unit (e.g. a radio that communicates using CDMA, GSM, GPRS or Bluetooth protocol according to standards such as IEEE 802.11a, 802.11b, 802.11g, or 802.11n), a power unit and a memory unit. The memory unit can include RAM, ROM, one or more hard drives, one or more flash drives or some other suitable data storage elements such as disk drives, etc.

The processing unit controls the operation of the remote processing device 108 or the remote cloud server 110 and can be any suitable processor, controller or digital signal processor that can provide sufficient processing power processor depending on the desired configuration, purposes and requirements of the system 100.

The display can be any suitable display that provides visual information. For instance, the display can be a cathode ray tube, a flat-screen monitor and the like if the remote processing device 108 or remote cloud server 110 is a desktop computer. In other cases, the display can be a display suitable for a laptop, tablet or handheld device such as an LCD-based display and the like.

System 100 can generally be used for detecting and tracking a user's heart rate. In some cases, system 100 may also track additional biometric features and other metrics for a user. In some cases, the user's detected heart rate may be used to determine various other biometrics for that user, such as energy expenditure for example. The user's heart rate as well as the additional biometric features and other metrics may be monitored, stored, and analyzed for the user. In different embodiments, aspects of the monitoring, storage and analysis of the different biometric features and other metrics may be performed by the wearable unit 102, a remote processing device 108, or the cloud server 110.

A remote cloud server 110 may provide additional processing resources not available on the wearable device 102 or the remote processing device 108. For example, some aspects of processing the bio-signals acquired by the sensors 106 may be delegated to the cloud server 110 to conserve power resources on the wearable device 102 or remote processing device 108. In some cases, the cloud server 100, wearable device 102 and remote processing device 108 may communicate in real-time to provide timely feedback to a user regarding their heart rate, other biometrics and any trends identified.

In some embodiments, system 100 may include a sensing unit with at least two sensors positioned to acquire a bio-signal from the user's skin surface. The at least two sensors may be positioned to acquire a differential bio-signal. In some cases, the sensors may be positioned cross-body to acquire the differential bio-signal. In such cases, a first sensor of the differential pair can be positioned on one side of the user's body while a second sensor of the differential pair can be positioned on the other side of the user's body (e.g. one electrode on the user's right bicep and one electrode on the user's left bicep). Each sensor can be connected to a differential input of the same differential amplifier. In some cases, the sensing unit may include a plurality of differential sensor pairs. The plurality of differential sensor pairs can be used in combination to extract a user's heart rate.

In some embodiments, wearable unit 102 may include a plurality of wearable devices. Each wearable device may include a skin-facing surface removably securable to the user's skin surface. In some cases, each of the wearable devices may communicate with each other or with remote processing device 108 or cloud server 110. The remote processing device 108, cloud server 110 or a controller of the wearable unit 102 may receive the captured electrical bio-signals from each wearable device (e.g. using a wireless communication module) and process them to determine the user's heart rate. Using a plurality of wearable devices 102 may facilitate cross-body or contralateral comparisons of the acquired bio-signals.

Figure 2:
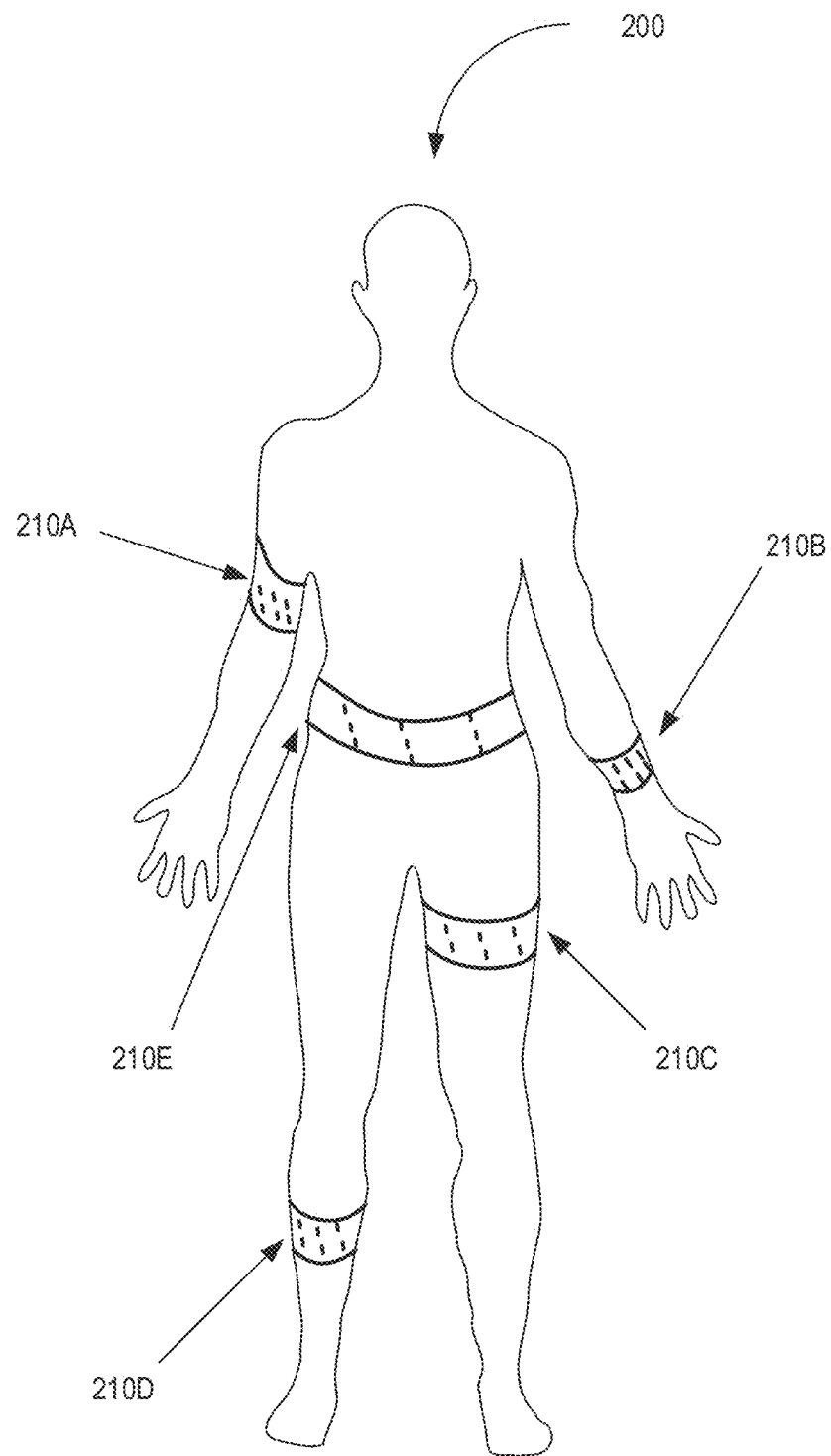
FIG. 2 is a diagram illustrating various examples of the placement on a user's body of a wearable device that can be used in the system of FIG. 1.

Referring now to FIG. 2, shown therein is a diagram 200 illustrating examples of locations where wearable devices 210a-210e may be removably secured to a user's skin surface. In some embodiments, one or more of wearable devices 210a-210e may be combined as a wearable unit that can be used to acquire electrical bio-signals from multiple locations on a user's body.

In diagram 200, wearable device 210a is secured to a user's skin surface near the user's bicep, wearable device 210b is secured to a user's skin surface near the user's forearm, wearable device 210c is secured to a user's skin surface near the user's thigh, wearable device 210d is secured to a user's skin surface near the user's lower leg, and wearable device 210e is secured to a user's skin surface around the user's hip bones and stomach. A skilled person will appreciate that other suitable placements may also be selected for a wearable device 210.

The quality of acquired bio-signals can be impacted by the type and location of sensor used. For example, activities involving muscle contractions, particularly in muscles near where the sensors are mounted may increase the amount of signal contamination. In some cases, bio-signals may be acquired from specific sites on the user's body to reduce the amount of undesired signals acquired. For example, sites with a limited amount of nearby muscle may be used.

In some cases, the particular placement of a wearable device 210 may be determined based on a particular activity being undertaken by an individual. In some cases, an individual may select a particular placement based on nearby muscle groups the individual wishes to track. For example, a user may select the thigh or lower leg when targeting different muscles in the legs, and the lower or upper arm when performing activities that target the muscles of the arms.

In other cases, the individual may select a particular placement because it is close to or distant from large muscle groups. For example, wearable device 210e is placed around the user's waist or hip. Sensors in wearable device 210e can be aligned with the user's hip bone. Placing wearable device 210e on regions without high intensity muscle activity, such as a user's hip bone, may facilitate the acquisition of bio-signals that are not highly contaminated by electrical signals generated by muscle activity such as EMG signals. Similarly, other regions of lower muscle activity may be desirable locations to place one or more sensors of a wearable device 210 to reduce the contributions from EMG signals when detecting a user's heart rate.

In some cases, the particular placement of a wearable device 210 may be dependent on the size or shape of that particular wearable device. For example, wearable device 210e that can be placed around a user's waist may be different from wearable devices 210d or 210b that can be placed around a user's calf or forearm respectively.

Where the heartbeat impulses are relatively dominant in the acquired bio-signals, standard finite impulse response (FIR) filtering, infinite impulse response (IIR) filtering, wavelet transforms, or matched filters in the form of the expected waveform, or wavelet transforms may be used to remove the contaminations and to detect the heartbeat impulses or signals indicative thereof. The heart rate can then be determined from the heartbeat impulses. In other cases, where the signal to noise ratio (SNR) is small, the heart beat impulses have similar frequency properties as the contaminant factors, or contaminations are significant, standard filtering may not be sufficient. Furthermore, voluntary or involuntary muscle contractions may contain similar frequency contents to the heart beat impulse signals.

In such cases, additional bio-signals may be recorded from other locations in the same limb or different limbs. For example, cross-body bio-signals may be acquired using a sensing unit having at least two sensors. In some cases, the acquired bio-signals may be differential signals. In some cases, polyphasic bio-signals may be acquired. The plurality of acquired bio-signals can be used in combination to detect the contaminated heartbeat impulses and measure the heart rate using predictive methods such as machine learning and pattern recognition processes.

Referring now to FIG. 3A, shown therein is a diagram of a plot 300 illustrating an example of an isolated heart beat PQRST complex. Plot 300 is a drawn example of the waveform generated by the bio-signals of a heartbeat impulse. The P wave is indicative of the polarization of an individual's atria, while the QRS complex represents the rapid depolarization of the individual's right and left ventricles. The T wave indicates the repolarization of the individual's ventricle. In some cases, a signal portion corresponding to one or more of the portions of the PQRST complex (e.g. the R wave or the S wave) may be used as a heartbeat impulse characteristic. For example, as mentioned above, a matched filter may be used to identify signal portions having such heartbeat impulse characteristics. Alternatively, a correlation coefficient of a moving window of the preprocessed bio-signal stream can be determined with respect to a template of a heartbeat impulse signal, such the PQRST complex shown in plot 300 or a subset thereof.

Figure 3B:
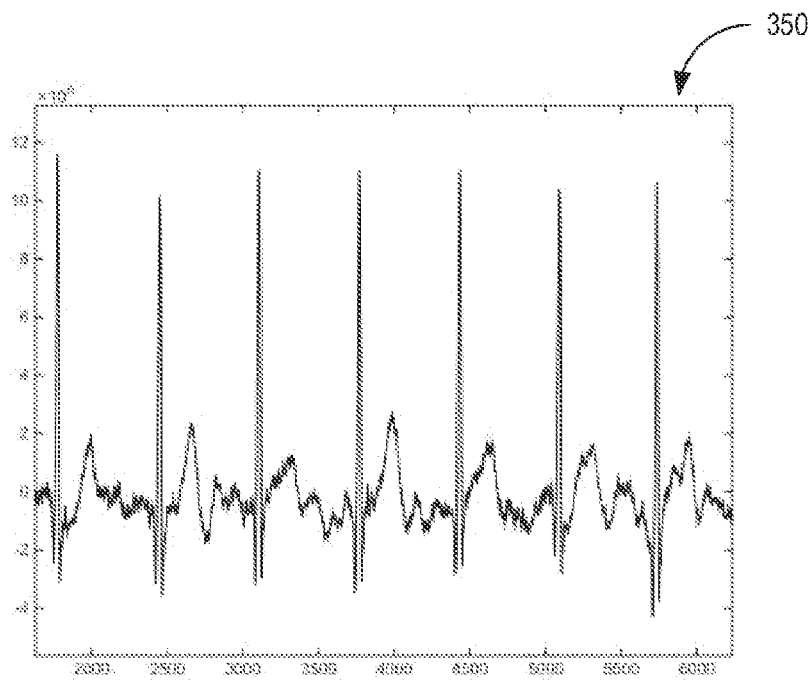
FIG. 3B is a diagram illustrating a plot of a series of example heart beats acquired using a rhythm strip placed on a user's chest.

Referring now to FIG. 3B, shown therein is an example plot 350 of a stream of bio-signals acquired from a healthy individual. The stream of bio-signals shown in plot 350 was acquired using surface sensors placed on the individual's chest. The stream of bio-signals in plot 350 show clearly the waveform generated by the individual's heart beat impulses. Bio-signals acquired from other locations of the individual's skin surface will typically contain contaminated and degraded traces of the heart beat impulse signals shown in plot 350.

Figure 4A:
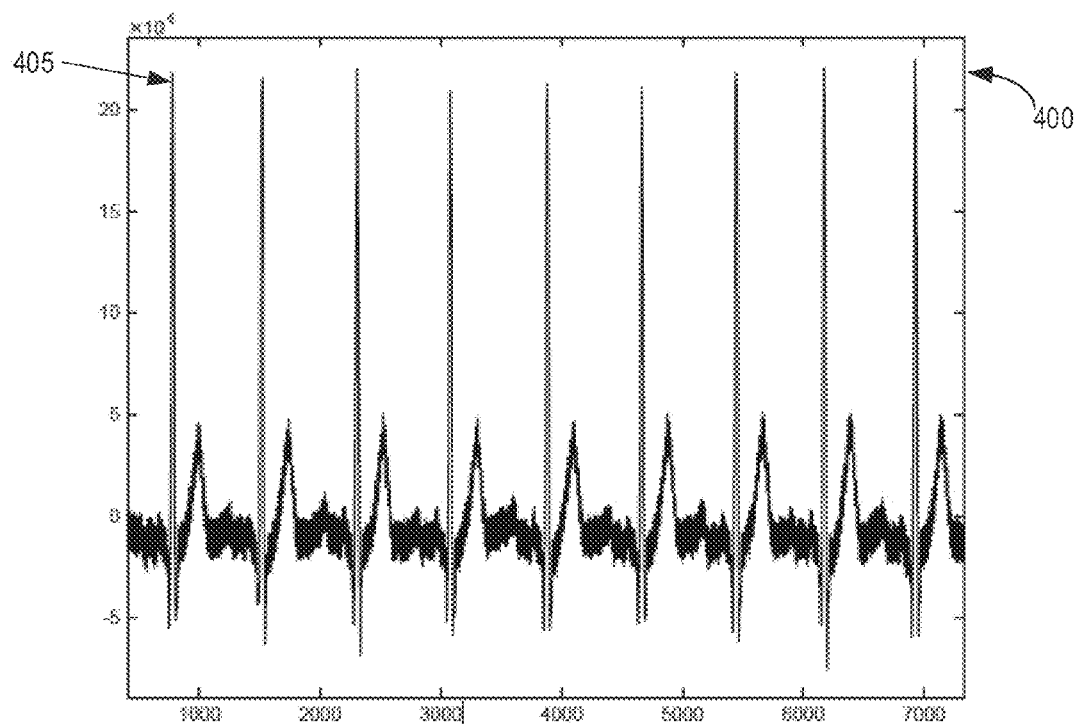
FIG. 4A is a diagram illustrating a plot of an example electrical bio-signal acquired from a user's lower stomach.

Referring now to FIG. 4A, shown therein is an example plot 400 of a stream of bio-signals acquired from a sensing unit with sensors placed on an individual's lower stomach. Plot 400 includes bio-signals indicative of the heart beat impulses as well as other undesired signal components such as noise. Nonetheless, the R waves 405 of the individual's heart beat impulses are still visibly apparent in plot 400.

Figure 4B:
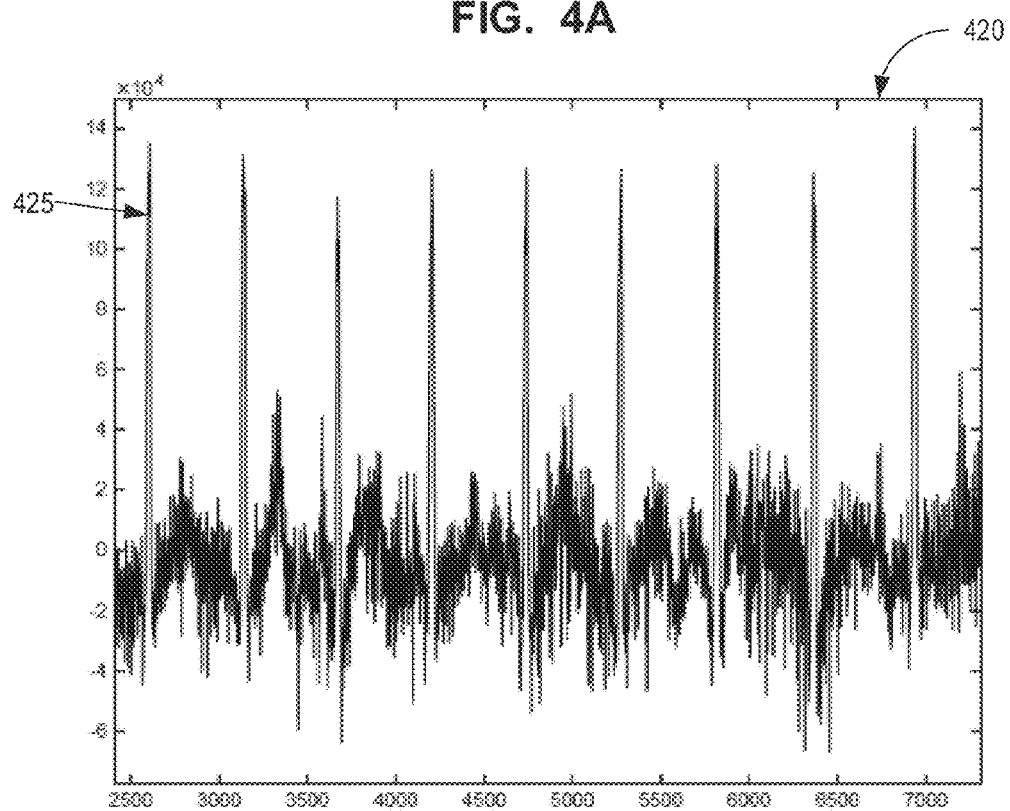
FIG. 4B is a diagram illustrating a plot of another example electrical bio-signal acquired from a user's lower stomach.

Referring now to FIG. 4B, shown therein is another example plot 420 of a stream of bio-signals acquired from a sensing unit with sensors placed on an individual's lower stomach. Plot 420 shows a higher level of background noise than plot 400 and plot 350. Nonetheless, the R waves 425 of the individual's heart beat impulses are still visibly detectable.

Figure 4C:
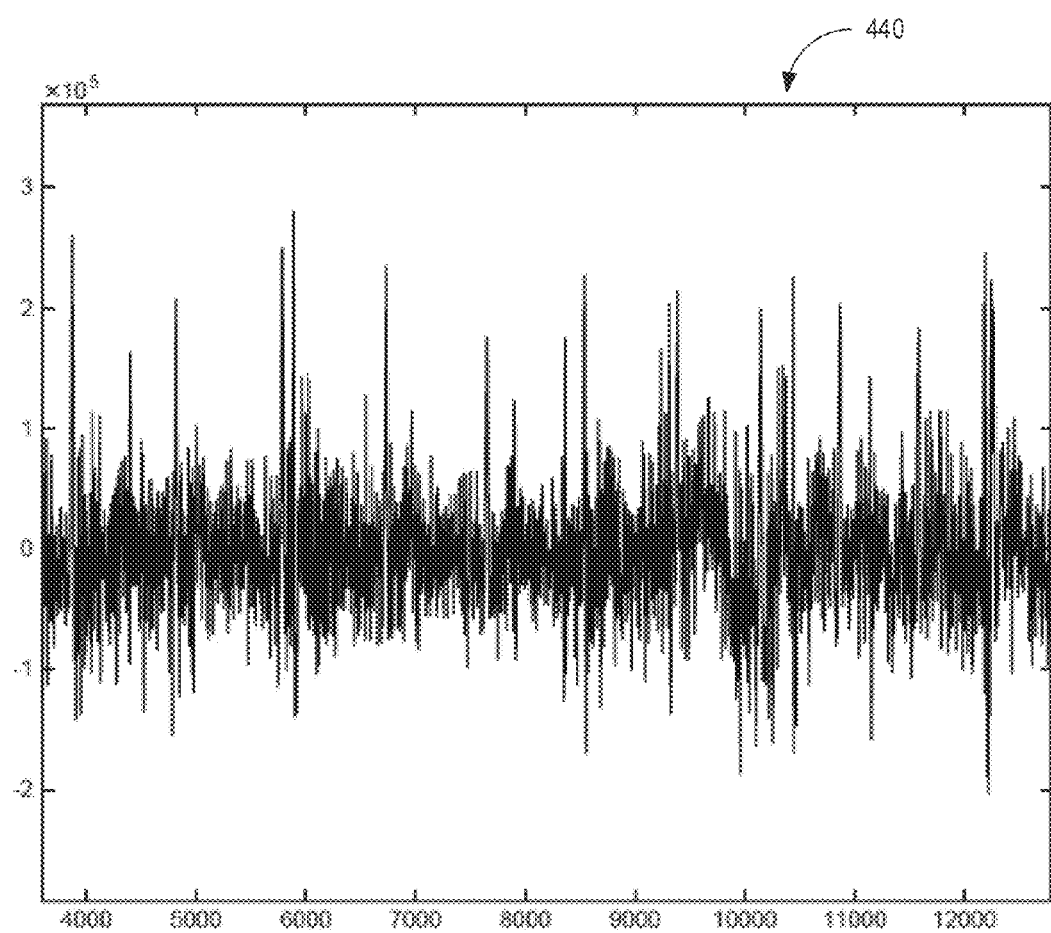
FIG. 4C is a diagram illustrating a plot of another example electrical bio-signal acquired from a user's lower stomach.

Referring now to FIG. 4C, shown therein is another example plot 440 of a stream of bio-signals acquired from a sensing unit with sensors placed on an individual's lower stomach. Plot 440 have even more significant contaminations than the acquired bio-signals shown in plot 400 and plot 420. In plot 440, the signal components corresponding to the heart beat impulses are visually undetectable because of the high level of background noise.

Figure 5:
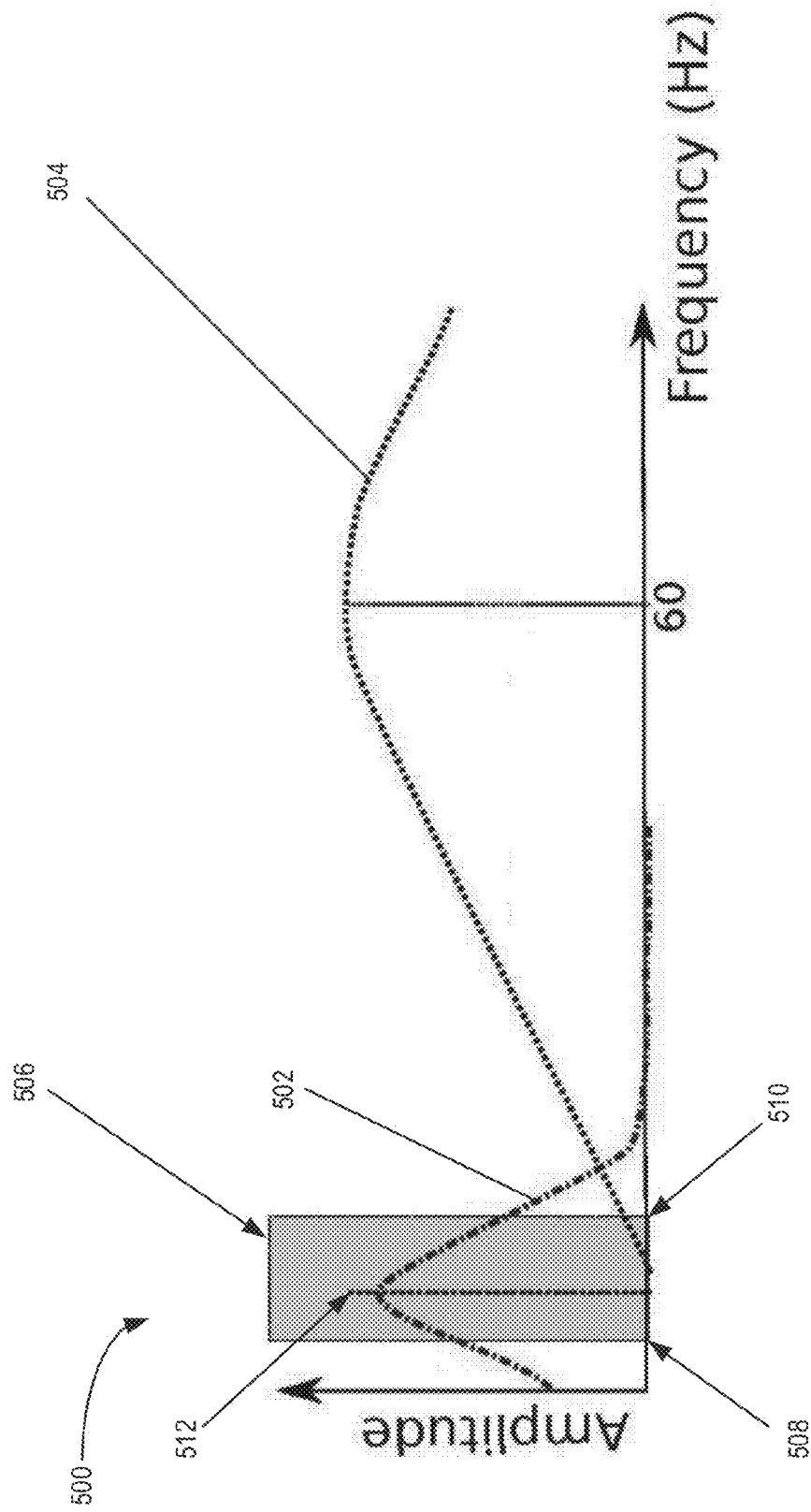
FIG. 5 is a diagram illustrating a power spectral density plot of an example heartbeat signal and electromyography signal.

Referring now to FIG. 5, shown therein is an example plot 500 showing the spectral density of an example heartbeat impulse signal 502 and an example electromyography signal 504 over a range of frequencies (from 0 Hz to greater than 60 Hz).

As shown in plot 500, the heartbeat impulse signal 502 is predominantly found in predetermined frequency range 506 that ranges from a lower cutoff frequency 508 to an upper cutoff frequency 510. The predetermined frequency range 506 is an example of a passband that may be chosen to filter an acquired electrical bio-signal in accordance with the teachings herein. The predetermined frequency range 506 is typically chosen to include a peak heartbeat frequency 512 that corresponds to the frequency at which the heartbeat impulse signal is expected to have the greatest amplitude.

In plot 500, lower cutoff frequency 508 has been selected as 3 Hz while upper cutoff frequency 510 has been selected as 10 Hz. This range includes the peak heartbeat frequency 512 (here shown as 5 Hz) while including minimal contribution from the EMG signal 504. Frequency range 506 also excludes power line hum noise at 60 Hz and may mitigate the effects of motion artifact noise by excluding lower frequency components.

Figure 6:
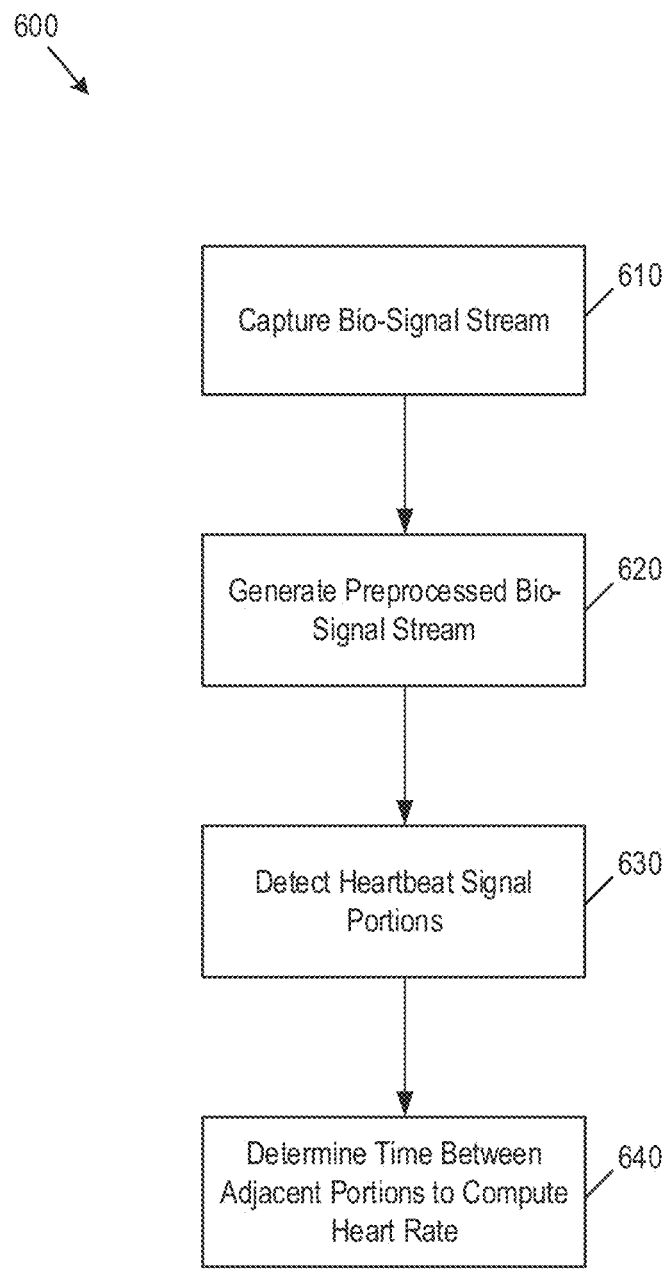
FIG. 6 is a flowchart illustrating an example embodiment of a method for determining a user's heart rate.

Referring now to FIG. 6, shown therein is an example embodiment of a method 600 for detecting a user's heart rate. In different embodiments, method 600 can be applied using various detection algorithms that can include either supervised or unsupervised heartbeat detection systems. The detection algorithms can generally be applied to determine heartbeat signal portions in a bio-signal stream corresponding to a heartbeat impulse. The time between adjacent heartbeat signal portions can then be determined to compute the user's heart rate.

Supervised detection algorithms may refer to machine learning methods where a predictive model is inferred based on labelled training data. The inferred predictive model may then be applied to unknown data to identify signal components indicative of the desired signal components, i.e. heartbeat impulse signals. Unsupervised detection algorithms can be used to identify signal components indicative of the desired signal components without having previously been trained using labelled data.

At 610, a bio-signal stream is captured. A controller can capture a bio-signal stream using at least one sensor provided in a sensing unit coupled to the controller, such as the sensing unit 102 shown in FIG. 1.

As discussed above, various types of sensors can be used to acquire the bio-signal stream such as various types of active and passive electrodes and other non-contact sensors. In some cases, one sensor can be used to capture a single-ended bio-signal stream. In other cases, at least two sensors can be used to capture the bio-signal stream. For example, the at least two sensors can be positioned to acquire a differential or polyphasic bio-signal from the user's skin surface.

In some cases, the at least two sensors may be placed at different locations spaced apart on the same limb or on the same side of a user's body. In other cases the at least two sensors can be placed cross-body (on opposite sides of the user's body) to acquire a differential bio-signal input. Spacing the at least two sensors apart may reduce the amount of overlap between the noise signals in the bio-signal streams acquired from each sensor. For example, where the sensors are placed cross-body the signals may be less likely to acquire overlapping EMG signals from the muscles on different sides of the body. This may improve the sensitivity and specificity of detecting signals indicative of the heart beat impulses.

At 620, the controller can generate a preprocessed bio-signal stream by filtering the captured bio-signal stream to remove undesired signal components. In many cases, the bio-signals streams captured at 620 can be contaminated by undesired signals components such as environmental noise, motion artifacts, and electrical signals from the user's muscles. Accordingly, a preprocessed bio-signal stream may be generated to minimize the contributions from these undesired signal components. For example, a band-pass filter may be applied to the captured bio-signal stream to generate a preprocessed bio-signal stream with frequency content predominantly from a heartbeat impulse signal.

In some cases, a band-pass filter may be applied with a passband in a region centered around 5 Hz. The passband may have a lower cutoff frequency in a range of 3 Hz to 5 Hz. In some cases, the passband may have an upper cutoff frequency in a range of 10 Hz to 18 Hz.

In some cases, other preprocessing techniques known in the art may be applied to the signal to reduce the contributions of the undesired signal components or to emphasize particular features of the bio-signal stream. In some cases, feature extraction, projection and selection methods can be used to extract information from the preprocessed bio-signals. Examples of features include signal mean value, maximum value, minimum value, median value, signal frequency content, and features identified using generative models. In some cases, the features can be manually selected while in other cases, features may be automatically identified using techniques such as analysis of variance (ANOVA).

In some cases, signal decomposition or projection methods such as independent component analysis (ICA), principal component analysis (PCA) and discrete wavelet transforms can be used, where the results or their subsets may directly correspond to the heartbeat impulses, or alternatively can provide a suitable feature set to be used with classifiers.

Linear discriminants (LDs) such as linear discriminant analysis (LDA) and Fisher's linear discriminant (FLD) can be used, in some cases alongside PCA and ICA for recognizing a linear combination of features. LD-based methods can be used to recognize different features within the observed data.

At 630, the controller can detect heartbeat signal portions when the preprocessed bio-signal stream has heartbeat impulse characteristics. Heartbeat signal portions may be determined using supervised or unsupervised detection methods.

In some cases, the controller may use a moving window to identify signal portions within the moving window having heartbeat impulse characteristics. The size of the moving window can be selected so that the moving window will always contain at least one signal portion corresponding to the heartbeat impulse. This may avoid false positives, for example where the threshold value is determined based on the amplitudes found in the moving window.

In some cases, the heartbeat impulse characteristics can be that the signal portion exceeds a threshold value. The controller may use the moving window to determine the signal portions exceeding the threshold value. The signal portions exceeding the threshold value may be indicative of a heart beat impulse.

Generally, the threshold value may be selected or tuned based on the spatiotemporal characteristics of the preprocessed bio-signal stream within the moving window. This tuning can be applied to account for the recent spatiotemporal properties of the preprocessed bio-signal stream. For example, where the preprocessed bio-signal stream has larger amplitude within the moving window, a larger threshold value may be determined. Similarly, where the preprocessed bio-signal stream has smaller amplitude within the moving window, a smaller threshold value may be determined. This can improve the accuracy of detecting heartbeat impulse signals as the level of the acquired electrical bio-signals change.

The controller may determine the threshold value using various linear or non-linear combinations or functions of the mean amplitude, median amplitude, maximum amplitude, minimum amplitude, or other spatiotemporal properties of the preprocessed bio-signal within the moving window. For example, the controller may determine the threshold value by identifying a maximum amplitude of the preprocessed bio-signal stream in the moving window. The controller may then identify a minimum amplitude of the preprocessed bio-signal stream in the moving window. The controller may determine the threshold value as a specific point between the minimum amplitude and the maximum amplitude. For example, the controller can compute a midpoint between the minimum amplitude and the maximum amplitude to determine the threshold value.

In some cases, detecting a heartbeat signal portion may include determining a spatiotemporal similarity between the signal portion and a heartbeat template. For example, a matched filter based on characteristics of the heartbeat template can be used to identify the heartbeat signal portions. In some cases, a correlation coefficient can be determined between signal portions in a moving window and the heartbeat template. Signal portions having a correlation coefficient greater than a heartbeat threshold can be identified as heartbeat signal portions.

In some cases, trained heartbeat detection systems can be used to identify the heartbeat signal portions. A detection algorithm may receive the preprocessed bio-signal stream as an input and identify heartbeat signal portions in the preprocessed bio-signal stream. The detection algorithm can use various pre-trained heartbeat detection systems to determine, for each sample (or a collection of samples) in the preprocessed bio-signal stream, whether that sample is in a signal portion corresponding to the desired signal component, i.e. a heartbeat impulse. In some cases, the detection algorithm may classify each sample into signal portions indicative of the heartbeat impulse and signal portions not indicative of the heartbeat impulse.

Various different predictive models and/or pattern recognition techniques may be used for the trained heartbeat detection system, such as hidden Markov models (HMM), K-nearest Neighbors models (KNN), Support Vector Machines (SVM), Artificial Neural Networks (ANN), Naive Bayes (NB), and other statistical models or classifiers for example.

The heartbeat detection systems may be pre-trained using a sample data set that includes a plurality of captured bio-signal streams. An example method for training a heartbeat detection system is described in more detail below with reference to FIG. 7.

In one example embodiment, the heartbeat detection system can use a pre-trained hidden Markov model to determine heartbeat signal portions in the preprocessed bio-signal stream. The loglikelihood values for each sample in the preprocessed bio-signal stream can be calculated using the pre-trained model and a detection algorithm such as the Viterbi algorithm, for example. The loglikelihood values may indicate the likelihood (according to the pre-trained model) that the samples are in a heartbeat signal portion. The Viterbi algorithm may be applied to the preprocessed bio-signal stream to determine a most likely sequence of signal inputs (i.e. signals contributing to the acquired bio-signal stream). This can be used to identify a most likely sequence of inputs, or signal components, corresponding to heartbeat impulse signals.

The loglikelihood values can then be used to determine the heartbeat signal portions of the preprocessed bio-signal stream. For example, signal portions having loglikelihood values above a threshold value may be determined to heartbeat signal portions. The threshold values may be determined as described above. In some cases, peaks of the loglikelihood values may be used to determine the heartbeat signal portions. In some cases, the loglikelihood values may be processed (e.g. smoothed) prior to determining the heartbeat signal portions).

At 640, the controller can determine the time between adjacent heartbeat signal portions to compute the user's heart rate. The time between adjacent signal portions can be computed in various ways, for example by determining the time between pre-defined fixed points of the adjacent signals portions. For example, the pre-defined points may be leading or trailing edges of a signal portion, or the mid-point, ⅓ of the length, ¼ point etc.

In some cases, the controller may determine the time between adjacent signal portions by segmenting the preprocessed bio-signal stream into signal portions exceeding the threshold value and signal portions not exceeding the threshold value. For example, a step function may be applied to the preprocessed bio-signal stream to distinguish the signal portions having heartbeat impulse characteristics from those that do not have heartbeat impulse characteristics.

The controller may then determine the time between adjacent heartbeats to determine the user's heart rate. The time between adjacent heartbeats can be determined by identifying the number of samples between the adjacent signal portions. The user's heart rate can then be determined based on the time between each sample, which can be determined based on the sampling rate. The number of samples between adjacent heartbeat signal portions can be determined from start to start, end to end, middle to middle, or any other predetermined point of the adjacent heartbeat signal portions.

Once the user's heart rate has been detected, it can be used in a variety of ways. For example, the user's heart rate can be provided as real-time feedback to the user or it can be stored for later viewing. The user's heart rate can also be used to determine other biometrics for the user, as mentioned above. The heart rate may also be used to determine heart rate specific biometrics such as heart rate variability for the user.

In some cases, where bio-signal streams are acquired from multiple locations on a user's body the electrical bio-signal streams from the different locations can be combined and analyzed as a combination to identify the heartbeat signal portions. In other cases, the bio-signal streams may be individually analyzed to identify potential heartbeat signal portions in each bio-signal stream, and the potential heartbeat signal portions from each bio-signal stream can be used to determine the heartbeat signal portions. For example, the potential heartbeat signal portions can be merged using averaging, voting, or other methods to identify the heartbeat signal portions having heartbeat impulse characteristics. The identified heartbeat signal portions can then be used to determine the user's heart rate as described above.

In some cases where bio-signal streams are acquired from multiple sensors, the number and combination of sensors that are most likely to result in the most accurate heart rate measurement can be selected. For example, the sensors may be selected based on an activity currently being undertaken by the user. In some cases, the activity may be automatically recognized based on signals received from the one or more sensors (potentially in combination with signals from other sensors such as an inertial measurement unit) using a pre-trained system. In some cases, the activity can be manually selected by a user prior to detection of the heart rate, and the number and combination of sensors can be determined based on the selected activity.

In some cases, where a user is performing intense activities with considerable muscle contractions, the difficulty of identifying the signal components corresponding to the heartbeat impulses may increase. If quasi-periodic activities are performed, a separate predictive model (such as those described above) can be used to determine temporal segments in the acquired electrical bio-signals in which the heartbeat impulses are more easily detected. This may be done based on the electrical bio-signal alone or in combination with other signals such as signals from an inertial measurement unit. The methods described herein may then be applied to the identified temporal segments to detect the user's heart rate.

Figure 7:
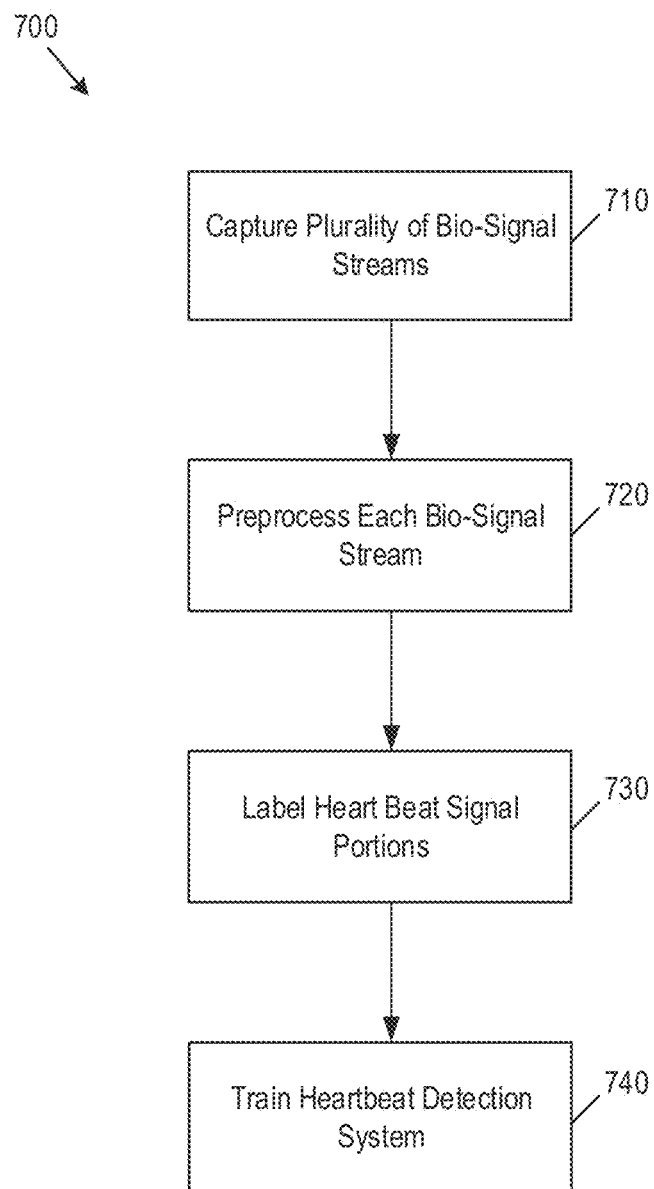
FIG. 7 is a flowchart illustrating an example embodiment of a method for training a heartbeat detection system to be used in the method of FIG. 6.

Referring now to FIG. 7, shown therein is an example method 700 of training a heartbeat detection system, which can be used to detect a user's heart rate, for example using method 600.

At 710, a sample data set including a plurality of bio-signal streams can be captured. In some cases, the plurality of bio-signal streams can be captured from one user, while in other cases bio-signal streams from a plurality of users may be captured. In some cases, the plurality of bio-signals stream may be retrieved from a storage module provided on cloud server 110 or on one or more remote processing devices 108. The plurality of bio-signal streams can be captured in the same manner as at step 610 of method 600, described above.

At 720, each bio-signal stream in the plurality of bio-signal streams can be preprocessed by a controller to generate a filtered bio-signal stream. The preprocessing performed at 720 can be similar to the preprocessing performed at 620, described above.

At 730, portions of the preprocessed bio-signal stream corresponding to heart beat impulses can be labelled. The labelling may be performed manually based on a visual inspection of each of the filtered bio-signal stream. For example, each of the filtered bio-signal streams may be reviewed and regions corresponding to a particular portion of the heartbeat impulse waveform (e.g. the R wave or S wave) may be identified.

At 740, a heartbeat detection system (e.g. a classifier or predictive model) for determining a user's heart rate can be trained using the labelled bio-signal streams from 730. The labelled bio-signal streams can be used as training data to generate a variety of supervised heartbeat detection systems. These detection systems can then be used, e.g., in method 600, to identify signal portions in acquired bio-signal streams that are more likely to correspond to a heartbeat impulse (i.e. heartbeat signal portions). The detections systems can be applied to streaming electrical signals to identify the heartbeat signal portions substantially in real-time.

In some cases, the heartbeat detection systems can be trained to identify heartbeat signal portions based on a plurality of electrical bio-signal streams acquired simultaneously from multiple sensors on a user's body. This can be done in accordance with method 700 using a sample data set that includes a plurality of bio-signal stream sets, where each set includes multiple bio-signal streams acquired simultaneously from different locations of a user's body. Such heartbeat detection systems can then be used to detect heartbeat signal portions in streaming electrical bio-signals acquired simultaneously from multiple locations on the user's body.

As mentioned above, various types of detection systems using techniques such as machine learning and pattern recognition can be used to generate heartbeat detection systems from the training data which can then be applied to acquired bio-signals using detection algorithms to determine heartbeat signal portions.

In some cases, feature extraction, projection and selection methods can be used to extract information from the pre-processed bio-signals during training method 700 as well. The extracted signal information can then be used to train the heartbeat detection systems at 740.

Figure 8A:
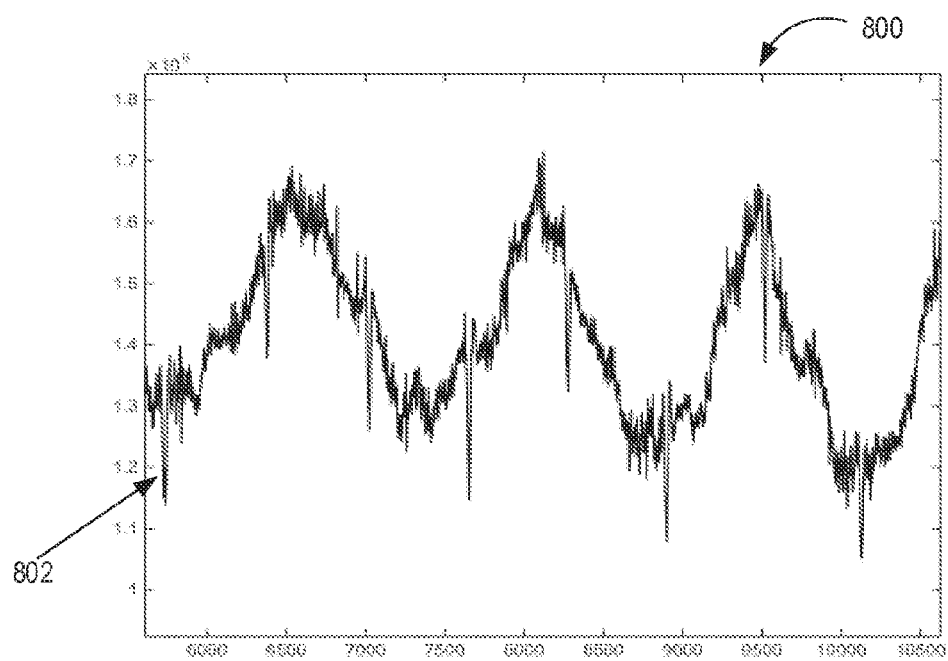
FIG. 8A is a diagram illustrating an example plot of a captured bio-signal stream.
Figure 8B:
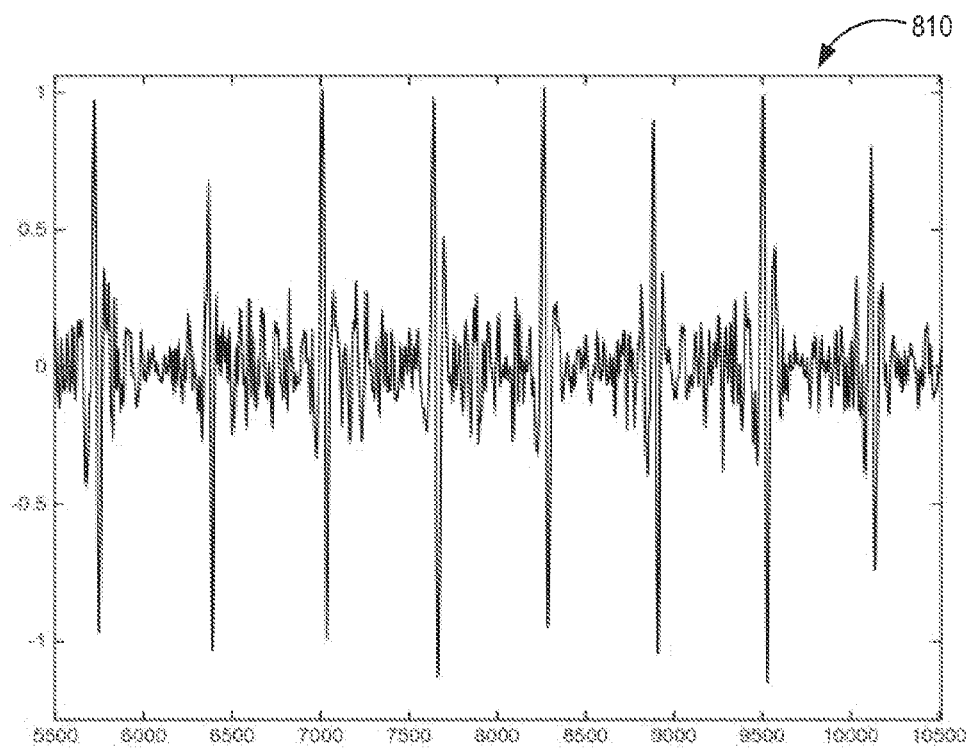
FIG. 8B is a diagram illustrating an example plot of a preprocessed bio-signal stream.
Figure 8C:
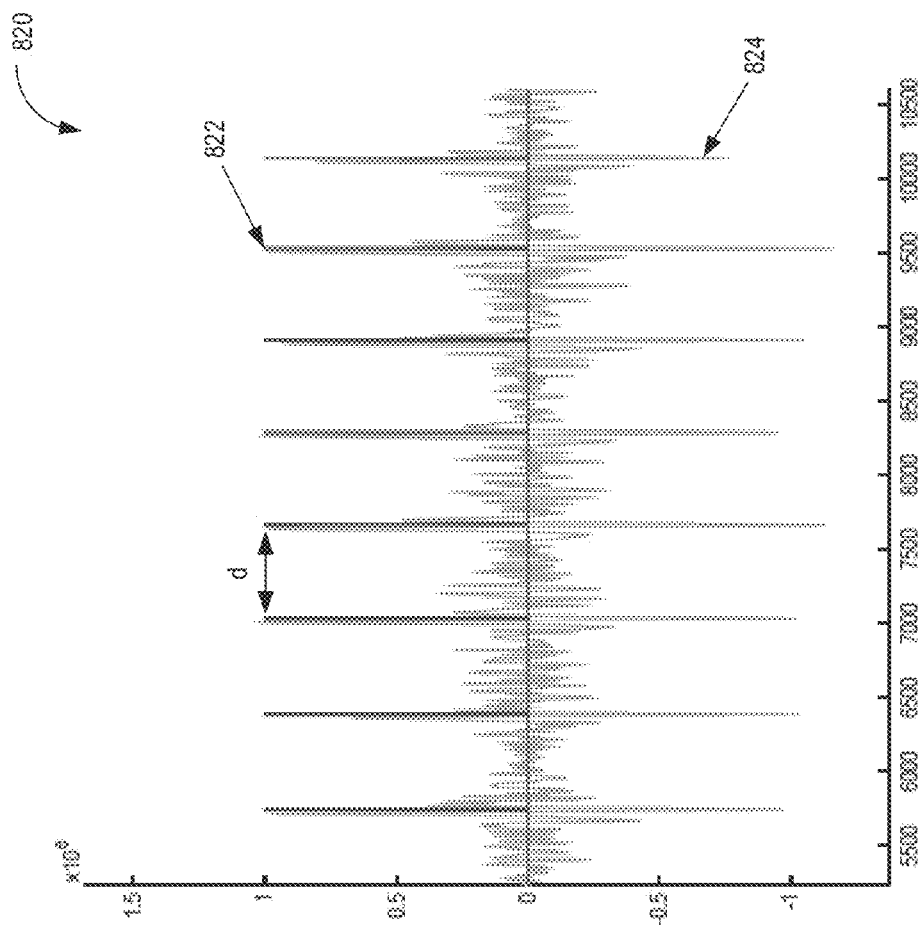
FIG. 8C is a diagram illustrating an example plot of a stream of heartbeat impulse signal portions detected using an embodiment of the method of FIG. 6 overlaid on the preprocessed bio-signal stream of FIG. 8B.

Referring now to FIGS. 8A-C, shown therein are plots showing the progression of a captured bio-signal stream as it is processed in an example embodiment of method 600. FIG. 8A shows a plot 800 of the bio-signal stream captured by a sensing unit having two sensors (here, contact electrodes were used) positioned cross-body, with one sensor placed on each hip bone of a user.

The bio-signal stream shown in plot 800 is a differential signal corresponding to the signals received from the two sensors. As mentioned above, the hip bones are regions without much muscle activity that would obscure the heartbeat impulse bio-signal. As a result, signal portions 802 in the unfiltered bio-signal provide a visual indication of heart beat impulse signals.

Referring now to FIG. 8B, shown therein is an example plot 810 of a preprocessed bio-signal stream. Plot 810 is an example of a signal that may be obtained at step 620 of method 600. The preprocessed bio-signal stream shown in plot 810 was obtained by applying a band-pass filter to the bio-signal stream shown in plot 800. In this case, the band-pass filter had an upper cut-off frequency at 10 Hz and a lower cut-off frequency at 4 Hz.

Referring now to FIG. 8C, shown therein is an example plot 820 of a segmented bio-signal stream 822 overlaid on the preprocessed bio-signal stream 824 of FIG. 8B having undergone a band-pass filter. The segmented bio-signal stream 822 shows an example of heartbeat signal portions identified using an embodiment of method 600 implemented using an unsupervised detection system. Segmented bio-signal stream 822 was obtained by applying a step function to the preprocessed bio-signal stream 824. The step function used to generate plot 820 used a threshold value that was set as the midpoint between the maximum amplitude and the minimum amplitude in a moving window.

A controller can determine a user's heart rate based on a segmented bio-signal stream such as stream 822. The distance, d, between adjacent heartbeat signal portions (shown by segmented bio-signal stream 822) can be measured in samples. The time between adjacent heartbeat signal portions, and thereby the heart rate, can then be computed using the sampling rate.

Figure 9:
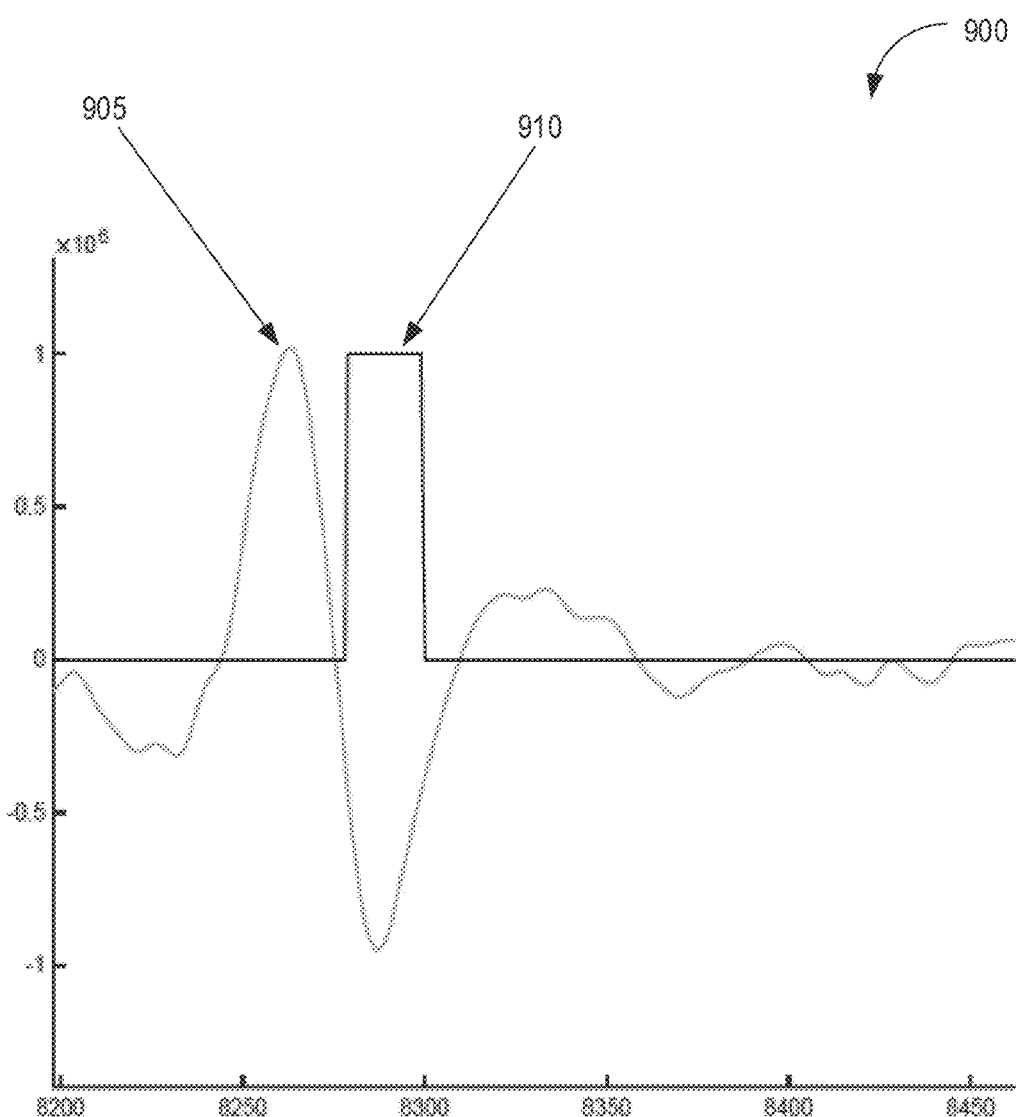
FIG. 9 is a diagram illustrating an example plot of a of a preprocessed bio-signal stream showing a heartbeat impulse region labelled in accordance with the method of FIG. 7.

Referring now to FIG. 9, shown therein is an example plot 900 of a preprocessed bio-signal stream 905 that has been labelled in accordance with the teachings of methods 700. Preprocessed bio-signal stream 905 is a filtered form of a differential bio-signal stream captured using cross-body sensors placed on the hipbone of a user. A label 910 indicating impulse region of preprocessed bio-signal stream having heartbeat impulse characteristics has been placed on plot 900 based on a visual inspection of plot 900. Labelled plot 900 can then be used to train a heartbeat detection system to identify signals indicative of a heartbeat impulse, as at 740.

Figure 10A:
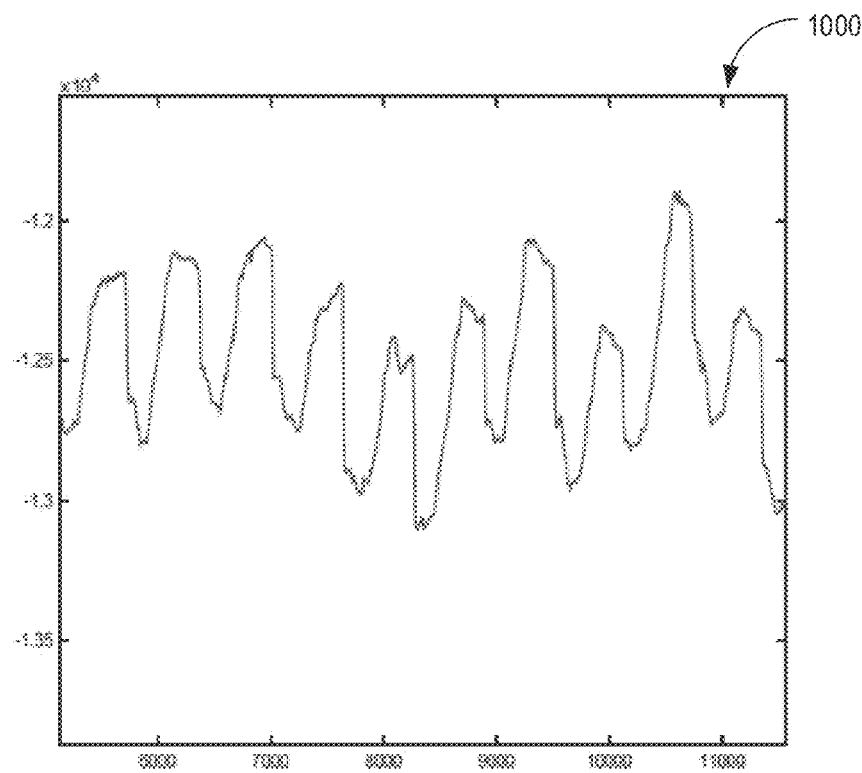
FIG. 10A is a diagram illustrating an example plot of the loglikelihood values generated in an example embodiment of the method of FIG. 6.

Referring now to FIG. 10A, shown therein is an example plot 1000 showing the loglikelihood values generated from a preprocessed bio-signal stream that has been preprocessed using a band-pass filter. The loglikelihood values in plot 1000 were generated by applying a Viterbi algorithm to the preprocessed bio-signal stream using a hidden Markov model trained in accordance with an embodiment of method 700.

Figure 10B:
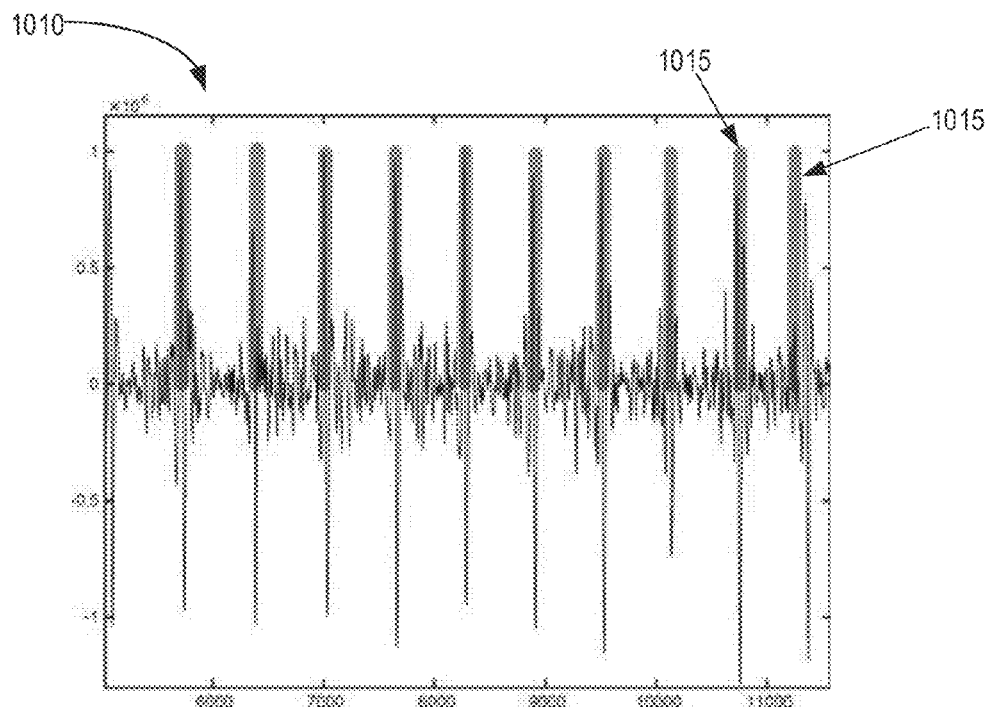
FIG. 10B is a diagram illustrating another example plot of a stream of detected heartbeat signal portions generated from the loglikelihood values of FIG. 10A overlaid on a filtered bio-signal stream.

Referring now to FIG. 10B, shown therein is an example plot 1010 showing heartbeat signal portions 1015 from the loglikelihood values of FIG. 10A. The heartbeat signal portions 1015 are overlaid on the filtered preprocessed bio-signal stream from which the loglikelihood plot 1000 was generated. The distance between adjacent heartbeat signals portions 1015 can be used to determine the user's heart rate, as explained above at 640.

While the applicant's teachings described herein are in conjunction with various embodiments for illustrative purposes, it is not intended that the applicant's teachings be limited to such embodiments. On the contrary, the applicant's teachings described and illustrated herein encompass various alternatives, modifications, and equivalents, without generally departing from the embodiments described herein.

The invention claimed is:

1. A system for detecting a heart rate, the system comprising:
   a sensing unit having a skin-facing surface removably securable to a user skin surface, the sensing unit having at least one sensor positioned to acquire a bio-signal from the skin surface; and
   a controller operatively coupled to the sensing unit, the controller configured to:
   capture an incoming bio-signal stream using the at least one sensor;
   band-pass filter the incoming bio-signal stream within a predetermined passband to produce a filtered bio-signal stream;
   pre-process the filtered bio-signal stream using a predictive model to determine a temporal segment of the filtered bio-signal stream in which heartbeat impulses are more easily detectable;
   in the temporal segment, process the filtered bio-signal stream in a moving window to determine heartbeat signal portions when the filtered bio-signal stream has heartbeat impulse characteristics; and determine time between adjacent heartbeat signal portions to compute the heart rate.

2. The system of claim 1, wherein the heartbeat signal portions are determined by applying a detection algorithm to the filtered bio-signal stream.

3. The system of claim 2, wherein the detection algorithm uses parameters of a supervised system trained using a plurality of captured bio-signal streams.

4. The system of claim 1, wherein the heartbeat impulse characteristics comprise the signal portion having spatiotemporal properties indicative of a heartbeat impulse.

5. The system of claim 1, wherein the heartbeat impulse characteristics comprise the signal portion exceeding a threshold value.

6. The system of claim 5, wherein the threshold value is determined using an amplitude of the filtered bio-signal stream in the moving window.

7. The system of claim 6, wherein the threshold value is determined as one of: a midpoint value, a mean value, a median value, a minimum value, a maximum value, a linear function, and a non-linear function of the amplitude of the preprocessed bio-signal stream in the moving window.

8. The system of claim 1, wherein the time between adjacent signal portions is determined by:

segmenting the filtered bio-signal stream into heartbeat signal portions having heartbeat impulse characteristics and signal portions not having heartbeat impulse characteristics;

determining the time between adjacent impulses.

9. The system of claim 1, wherein the passband has an upper cutoff frequency in a range between 10 Hz and 18 Hz.

10. The system of claim 1, wherein the passband has a lower cutoff frequency in a range between 3 Hz and 5 Hz.

11. The system of claim 1, wherein the sensors comprise electrodes.

12. The system of claim 11, wherein the electrodes are passive electrodes.

13. The system of claim 11, wherein the electrodes are active electrodes.

14. The system of claim 1, wherein the at least one sensor comprises two sensors.

15. The system of claim 14, wherein the sensors are positioned to acquire a differential bio-signal from the skin surface.

16. The system of claim 14, where the sensors are positioned cross-body.

17. The system of claim 1, wherein the filtered bio-signal stream comprises a quasi-periodic noise signal, and wherein pre-processing the filtered bio-signal stream comprises detecting the quasi-periodic noise signal.

18. The system of claim 17, wherein the quasi-periodic noise signal comprises an EMG signal.

19. A method for detecting a heart rate using a sensing unit having at least one sensor positioned to acquire a bio-signal from the skin surface, the method comprising:

capturing an incoming bio-signal stream using the at least one sensor;

band-pass filtering the incoming bio-signal stream within a predetermined passband to produce a filtered bio-signal stream;

pre-processing the filtered bio-signal stream using a predictive model to determine a temporal segment of the filtered bio-signal stream in which heartbeat impulses are more easily detectable;

in the temporal segment, processing the filtered bio-signal stream in a moving window to determine heartbeat signal portions when the filtered bio-signal stream has heartbeat impulse characteristics; and determining time between adjacent heartbeat signal portions to compute the heart rate.

20. A wearable device for detecting a heart rate, the device comprising:

a skin-facing surface removably securable to a user skin surface;

at least one sensor positioned to acquire a bio-signal from the skin surface; and a controller operatively coupled to the at least one sensor, the controller configured to:

capture an incoming bio-signal stream using the at least one sensor;

band-pass filter the incoming bio-signal stream within a predetermined passband to produce a filtered bio-signal stream;

pre-process the filtered bio-signal stream using a predictive model to determine a temporal segment of the filtered bio-signal stream in which heartbeat impulses are more easily detectable;

in the temporal segment, processing the filtered bio-signal stream in a moving window to determine heartbeat signal portions when the filtered bio-signal stream has heartbeat impulse characteristics; and determine time between adjacent heartbeat signal portions to compute the heart rate.

* * * * *